United States Patent [19]

McMahon et al.

[11] Patent Number: 5,310,650
[45] Date of Patent: May 10, 1994

[54] METHOD AND DEVICE FOR IMPROVED REACTION KINETICS IN NUCLEIC ACID HYBRIDIZATIONS

[75] Inventors: Michael E. McMahon, Libertyville; Julian Gordon, Lake Bluff, both of Ill.

[73] Assignee: Abbott Laboratoires, Abbott Park, Ill.

[21] Appl. No.: 925,322

[22] Filed: Aug. 4, 1992

Related U.S. Application Data

[63] Continuation-in-part of Ser. No. 324,926, Mar. 17, 1989, abandoned, which is a continuation-in-part of Ser. No. 912,878, Sep. 29, 1986, Pat. No. 4,960,691.

[51] Int. Cl.$^5$ .............................................. C12Q 1/68
[52] U.S. Cl. ........................................ 435/6; 435/287;
435/291; 435/299; 435/301; 435/310; 435/810;
436/501; 536/22.1; 536/23.1; 536/24.31;
536/24.32; 536/24.33; 935/78
[58] Field of Search .................. 435/6, 810, 287, 291,
435/299, 301, 310; 436/501; 536/27, 22.1, 23.1,
24.31-24.33; 935/78

[56] References Cited

U.S. PATENT DOCUMENTS

| 4,299,916 | 11/1981 | Litman et al. | 435/6 |
| 4,358,535 | 11/1982 | Falkow et al. | 435/5 |
| 4,787,963 | 11/1988 | MacConnell | 206/180.1 |
| 4,806,311 | 2/1989 | Greenquist | 422/56 |
| 4,960,691 | 10/1990 | Gordon et al. | 435/6 |

FOREIGN PATENT DOCUMENTS

| 163220 | 12/1985 | European Pat. Off. . |
| 167366 | 1/1986 | European Pat. Off. . |
| 0191640 | 8/1986 | European Pat. Off. . |
| 278220 | 8/1988 | European Pat. Off. . |
| 281390 | 9/1988 | European Pat. Off. . |
| 288737 | 11/1988 | European Pat. Off. . |
| WO84/02721 | 7/1984 | PCT Int'l Appl. . |
| WO86/07387 | 12/1986 | PCT Int'l Appl. . |
| WO88/08036 | 10/1988 | PCT Int'l Appl. . |

OTHER PUBLICATIONS

Jeppessen (1971) Biochem., J., vol. 124, pp. 357-366.
Brownlee et al. (1969) Eur. J. of Biochem., vol. 11, pp. 395-399.
Domdey et al. (1979) Anal. Biochem., vol.98, pp. 346-352.

Primary Examiner—Margaret Parr
Assistant Examiner—Ardin H. Marschel
Attorney, Agent, or Firm—Thomas D. Brainard

[57] ABSTRACT

The present invention relates to methods and test strips for performing nucleic acid hybridizations on a porous chromatographic material having the capacity for rapid chromatographic solvent transport of non-immobilized reagents and reactive solution components by means of a selected chromatographic solvent. The strip includes a first end or contact site, at which chromatographic solvent transport begins, a second end, at which chromatographic solvent transport ends, and at least one zone positioned between the first and second ends. The zone is impregnated with a capture nucleotide sequence which is immobilized against solvent transport and which is capable of hybridization with a complementary nucleotide sequence or probe so as to render it immobilized in the capture zone. The strip may further include a probe zone between the first end and the capture zone, wherein a labeled probe is impregnated such that it is mobilized by the solvent and transported to the capture zone where hybridization can occur. Interfering sample components and unhybridized nucleic acids are cleared from the capture zone by chromatographic solvent transport to form an inherent wash.

34 Claims, 3 Drawing Sheets

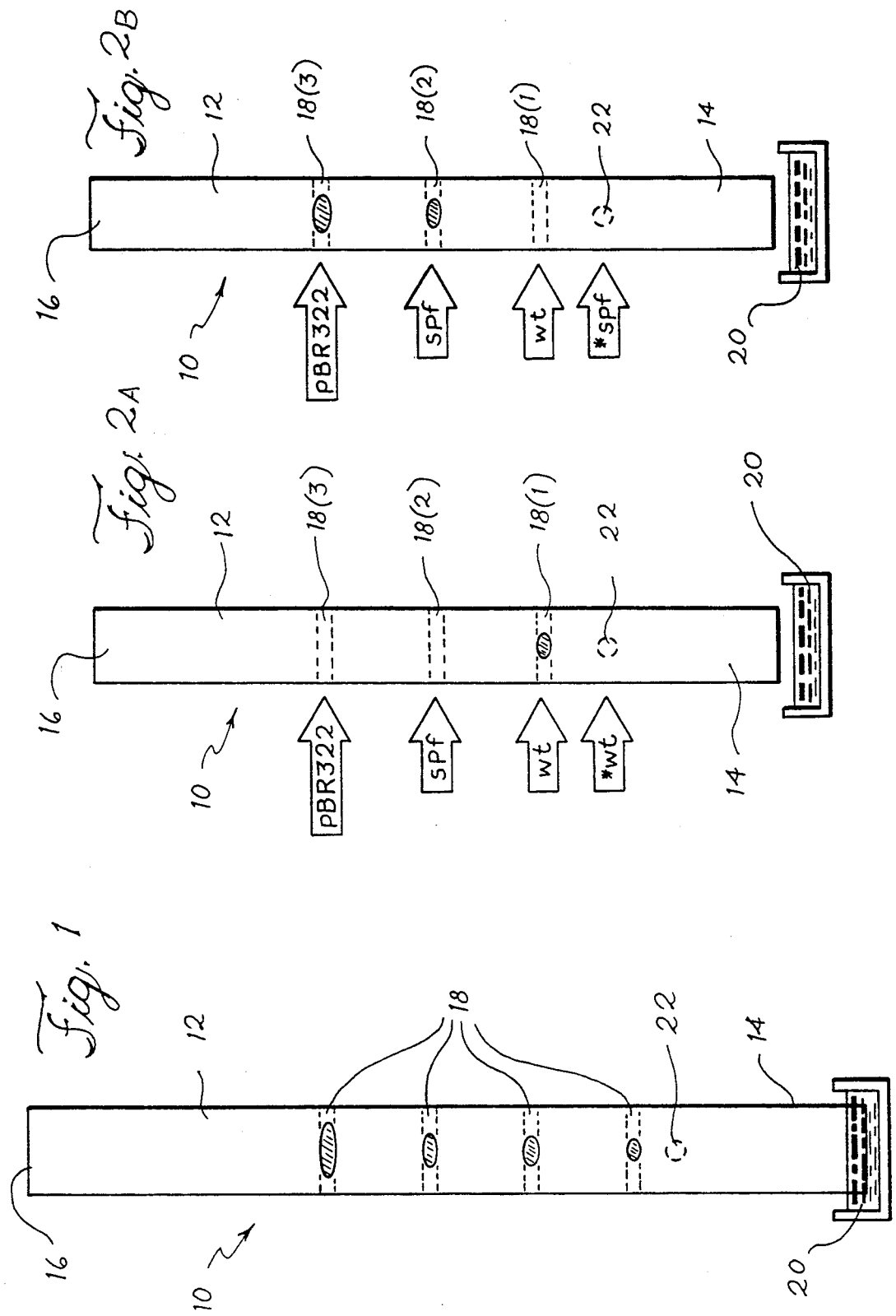

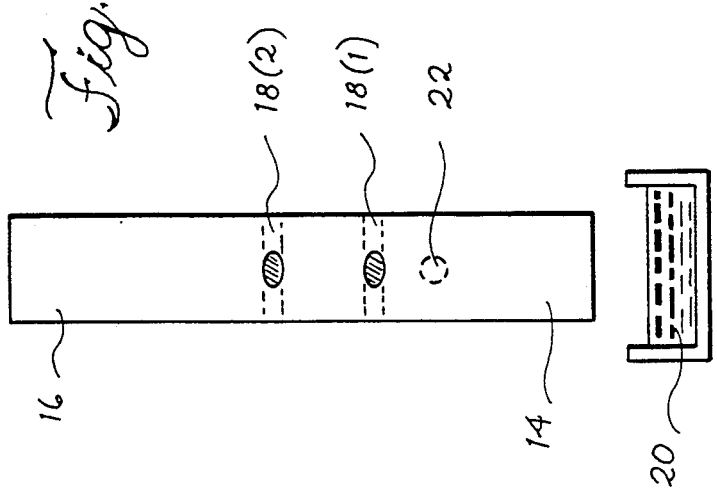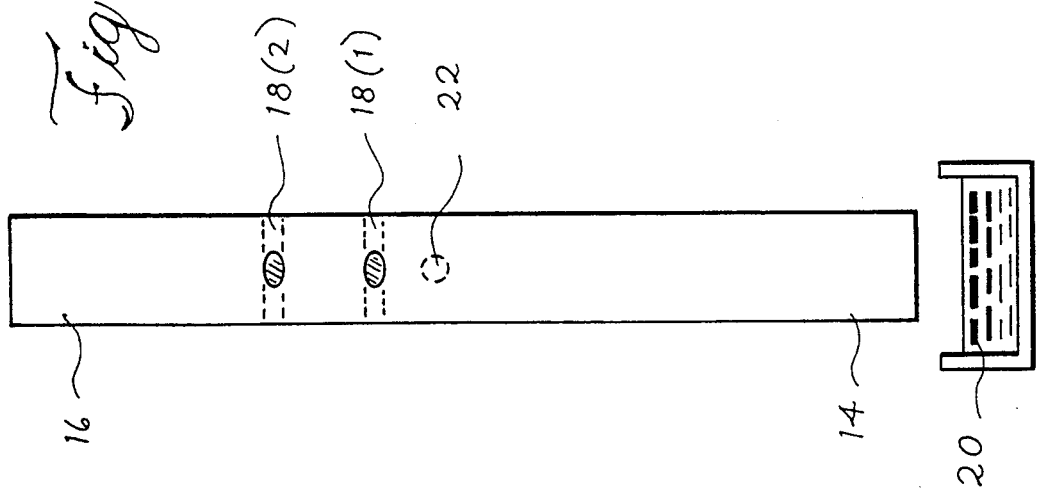

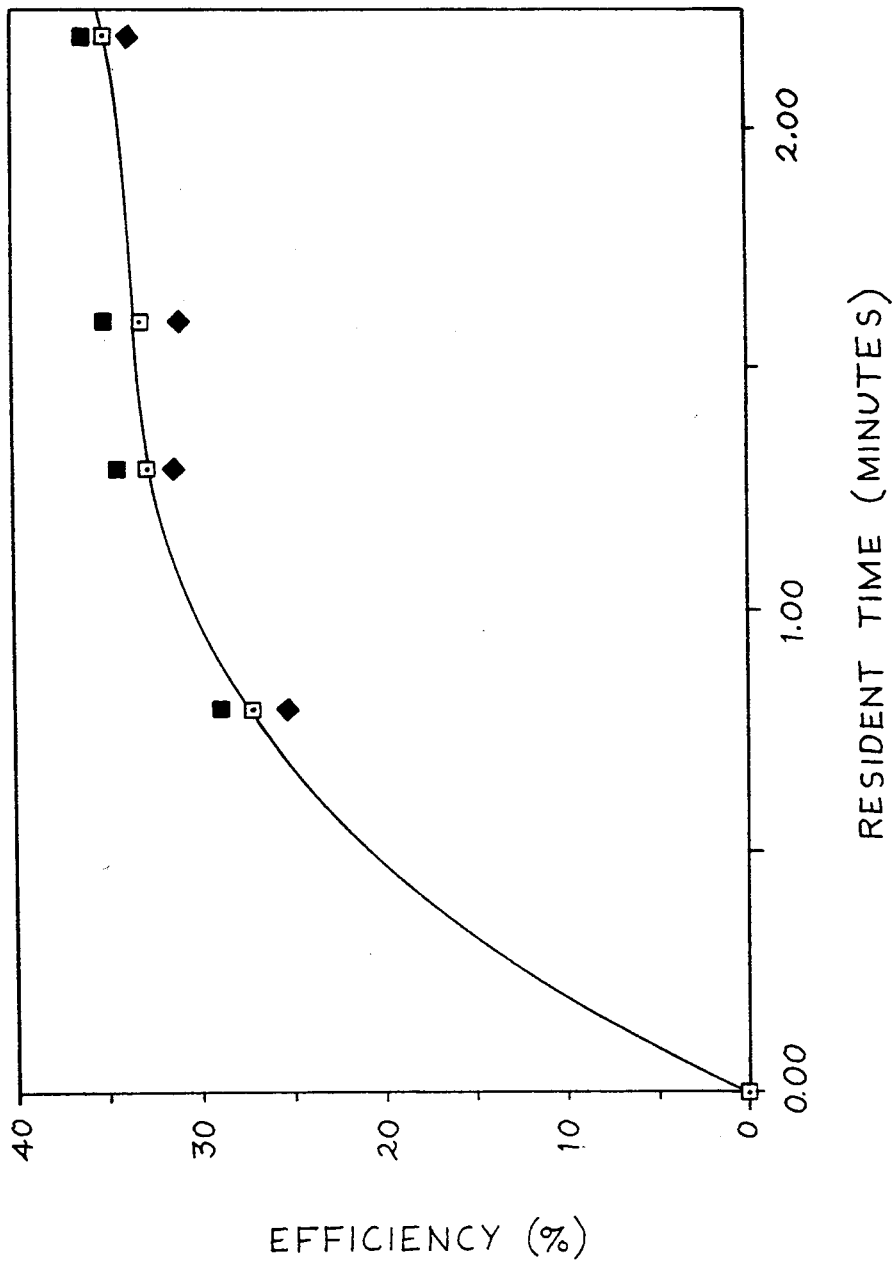

METHOD AND DEVICE FOR IMPROVED REACTION KINETICS IN NUCLEIC ACID HYBRIDIZATIONS

This application is a continuation of application Ser. No 07/324,926, filed Mar. 17, 1989, hereby abandoned, which is a continuation-in-part of application Ser. No. 912,878, filed Sep. 29, 1986, now U.S. Pat. No. 4,960,691.

BACKGROUND OF THE INVENTION

The present invention relates generally to solid phase methods for conducting specific binding assays and more specifically to the use of chromatographic techniques in conducting nucleic acid hybridization assays.

The use of specific binding assays has been found to be of great value in a variety of clinical applications. Various biological fluids and tissue samples can be analyzed for a wide variety of components such as drugs, hormones, enzymes, proteins, antibodies, DNA and RNA fragments and other biological material.

Specific binding assays include those assays wherein an analyte is measured which is a member of a specific binding pair consisting of a ligand and a receptor. The ligand and the receptor are related in that the receptor specifically binds to the ligand, being capable of distinguishing the ligand from other sample constituents having similar characteristics. Immunological assays depend on reactions between immunoglobulins (antibodies) which are capable of binding with specific antigenic determinants of various compounds and materials (antigens). Specific binding assays may also involve nucleic acid hybridization reactions wherein single strands of oligo or polynucleotides (e.g. DNA or RNA) hybridize through hydrogen bond formation with strands of other polynucleotides comprising complementary base sequences. Still other specific binding assays are known, such as those involving hormone receptors and biotin avidin, which involve neither immunological reactions nor hybridization.

Various types of specific binding assay techniques are also known for the detection of specific nucleic acid sequences. Such assays utilize nucleic acid hybridization procedures wherein complementary polynucleotide sequences of single stranded nucleic acid polymers recognize each other (nucleate) and interact (anneal) to form a stable duplex structure.

Nucleic acid hybridizations have been carried out in both homogeneous (in-solution phase) media and heterogeneous (solution/solid phase) media. See, for example, EP A-288 737, W086/07387 and U.S. Pat. No. 4,787,963. In homogeneous media, the hybridized polynucleotide sequences typically are separated from the unhybridized sequences by passing them over a hydroxyapatite column under appropriate conditions. Separation can also be achieved by gel exclusion as taught in Kuhns, EP A-278,220; by polycationic binding supports as taught in EP-A-281-390; or by precipitating agents as taught in EP-A-167,366. Several references teach heterogeneous hybridizations, including a sandwich hybridization taught by Ranki, et al., U.S. Pat. No. 4,563,419.

Despite the great advances that have been made with respect to specific binding assay techniques in recent years, there still remain significant opportunities for improvement of these techniques, particularly where nucleic acid hybridizations are concerned. Current solution phase hybridization procedures require significant incubation times, typically on the order of several hours, to permit diffusion and nucleation of complementary sequences. Even under known methods for acceleration of hybridization, incubations require about 1-2 hours. Then a separation step is required to separate the duplexes. Solid phase hybridizations make separation easier but often involve increased incubation times. Since only one of the two complementary nucleic acids is able to diffuse freely, diffusion and nucleation does not occur as rapidly at the surface of the solid phase.

MacConnell, U.S. Pat. No. 4,787,963 discloses a method and apparatus for improving the kinetics of heterogeneous hybridizations. By electrophoretically concentrating nucleic acid probes at a membrane to which the target sequences are bound, the chances of nucleation and annealing are increased. The reference claims hybridization occurs in a matter of 15-30 minutes, rather than hours.

EP A 0 288 737 discloses another method for achieving more rapid heterogeneous hybridizations. The time required for diffusion of sequences to the internal pores of a nitrocellulose membrane to which probe is bound necessitates longer incubation times. Therefore, the reference discloses a solid phase comprising water suspensible microparticles to which probe is bound. The decreased diffusion distances permit nucleation in about 30 minutes, and the separation of microparticles is easily accomplished by filtration.

Nevertheless, new systems involving solid phase assay devices having improved kinetics are highly desired. Such devices would preferably be simple to use in conducting assays for a wide variety of nucleic acids and would be capable of providing for hybridization in less than 15-30 minutes.

SUMMARY OF THE INVENTION

The present invention provides novel methods and devices for conducting nucleic acid hybridizations. These methods and devices require a minimum of washing and addition steps and are useful in rapidly carrying out qualitative and quantitative specific binding assays for a variety of analytes, including but not limited to, antibodies, antigens, DNA sequences, RNA sequences and other reactive chemical substances.

In particular, the present invention relates to a method of performing hybridization of nucleotide sequences on a solid phase, comprising:

a) on a porous medium capable of transporting a solution by capillarity, immobilizing a single stranded nucleotide sequence at a site remote from a contact site of the medium; and b) under hybridizing conditions, contacting the remote site with a solution containing or suspected of containing a complementary nucleotide sequence, the complementary nucleotide sequence being transported by capillarity to the remote site, whereby hybridization can occur between complementary base pairs of the nucleotide sequences.

In another aspect, the invention relates to a device for performing solid phase hybridizations of soluble, single stranded nucleotide sequences, comprising a porous medium having: a contact site; a site remote from the contact site whereat a single stranded nucleotide sequence complementary to a predetermined soluble nucleotide sequence is immobilized; and capillary means for transporting a solution containing the predetermined soluble nucleotide sequence under hybridizing conditions to the remote site, whereby hybridization can occur between complementary base pairs of the nucleotide sequences.

Surprisingly, it has been found that porous media, such as microporous media, are particularly well suited for rapid chromatographic transport and hybridization of oligo- and polynucleotide sequences, proteins and large polypeptides including antibodies and various antigens. It has been found that rapid chromatographic solvent transport of such materials is possible when non-specific binding sites of the substrate have been suitably blocked. Nucleic acid hybridization on such chromatographic media offers significant advantages in efficiency and ease of use. Hybridizations occur rapidly at the solvent front and separation is inherent as the mobile phase is transported through the solid phase. The use of microporous media is particularly preferred because of the improved speed and resolution afforded by the use of such materials.

Preferred devices according to the invention comprise a strip of porous chromatographic material having the capacity for rapid chromatographic solvent transport of non immobilized reagents and reactive sample components by means of a selected chromatographic solvent. The strip includes a contact site at a first end at which chromatographic transport begins, a second end at which chromatographic transport ends and at least one remote (capture) site positioned between the two ends where a capture nucleotide sequence is immobilized.

The complementary nucleotide sequence may originate in the chromatographic solvent. In this case, the solvent, including the complementary nucleotide sequence, wicks from the contact site to the remote site. Alternatively, the complementary nucleotide sequence originates on the strip itself, at a location (probe site) between the contact site and the remote (capture) site. In this case, the solvent starts at the contact site, wicks to the location of the complementary nucleotide sequence, mobilizes it and transports it to the remote site where hybridization can occur. The complementary nucleotide sequence or the hybridized duplex is detectable by some detection means, typically including a label of some sort. A convenient detection means is a complementary nucleotide sequence that is directly labeled with a radioisotope, such as $^{32}P$.

It further becomes possible to utilize multiple chromatographic solvent transport pathways such that the complementary nucleotide sequence and any other materials such as indicator or detector reagents can be transported according to a prearranged sequence, optionally with their separation maintained along partially non-coincident chromatographic solvent transport pathways. Multiple pathways may be formed so as to construct liquid microcircuitry which can be "programmed" to carry out a variety of multistep assay procedures by the sequential chromatographic solvent transport of various reagents to particular locations.

BRIEF DESCRIPTION OF THE DRAWINGS

FIG. 1 is a diagram of a strip showing several hybridization capture zones;

FIGS. 2A and 2B represent tow strips showing the specificity of hybridization using oligonucelotide probes differing by only one base;

FIGS. 3A and 3B two strips showing the equivalence of kinetics at capture zones of different distances from the bottom end of the strip; and FIG. 4 is a graphic representation of the efficiency data from Table II (Example 4).

DETAILED DESCRIPTION OF THE INVENTION

The present invention relates to methods and devices for achieving nucleic acid hybridizations in porous media, particularly in microporous chromatographic media. It has been found that the methods and devices of the present invention provide for rapid hybridization of complementary nucleotide sequences, without significant loss in hybridization efficiencies or in ease of separation. Moreover, by relying on the chromatographic solvent transport of reagent materials previously deposited upon the porous media, it is possible to avoid numerous addition and wash steps required in prior art assay systems. The solvent front passing through the solid phase serves as an inherent wash and removes unbound materials from the zones.

Devices

As shown generally in FIGS. 1-3, devices 10 according to the invention comprise a substrate or medium of porous chromatographic material having the capacity for chromatographic solvent transport of non-immobilized reagents and materials. The chromatographic media, which is described in more detail below, is generally a strip 12 having a first end or contact site 14 at which chromatographic solvent transport begins, a second end 16 at which chromatographic solvent transport ends, and at least one remote site or zone (third zone) 18 positioned between the first and second ends. (For consistency and ease of comparison with the parent application, the corresponding terminology from the parent application is herein given in parentheses.)

The remote zone 18, also referred to herein as a capture zone, is impregnated with a capture nucleotide sequence (second reagent) which is immobilized against solvent transport. The capture nucleotide sequence is also referred to as "capture sequence" or "capture reagent" and it is capable of hybridization with a complementary nucleotide sequence or probe (first reagent) so as to render it immobilized in the capture zone 18.

The strip 12 is contacted at the contact site (first end) 14 with a solvent 20 and the solvent forms the mobile phase front which wicks up the strip towards the second end 16. Upon arrival of the solvent front at the capture site 18, it will contain the soluble complementary sequence so that hybridization can occur when chromatographed under hybridization conditions.

The complementary nucleotide sequence may originate in the chromatographic solvent 20. In this case the solvent, including the complementary nucleotide sequence, wicks from the contact site to the capture site. Alternatively, the complementary nucleotide sequence originates on the strip itself, at a probe zone (first zone) 22 between the contact site and the capture site. In this case, the solvent starts at the contact site, wicks to the probe zone 22, mobilizes the complementary nucleotide sequence and transports it to the remote site where hybridization can occur.

A second important aspect of the invention is that interfering substances and non analyte components of the solvent which might cause inappropriate binding of the probe complementary nucleotide sequence at the capture zone are removed therefrom by solvent transport. This feature, whereby a wash step is inherently carried out upon the capture zone eliminates the step of manually washing that zone after application of the complementary nucleotide sequence. Elimination of this wash step also makes it possible to pre-apply chromatographically mobile reagent materials such as the probe or other reagent materials (ie. detection means) to the strip material before running the solvent in the course of the assay procedure.

Sandwich hybridizations may also be performed according to the invention, wherein an "analyte" consists of a strand of DNA or RNA with a specific nucleotide sequence. The capture reagent can be a single stranded DNA or RNA probe immobilized to the strip material which presents a nucleotide sequence capable of hybridizing with a first portion of the analyte nucleotide sequence so as to immobilize the analyte. The complementary nucleotide sequence can then be a labelled specific binding material such as a labelled DNA or RNA probe with a nucleotide sequence capable of hybridizing with a second proximate portion of the analyte nucleotide sequence so as to be immobilized by the analyte.

As shown in FIG. 2B, it should be understood that the capture zone may comprise one or more sites each having immobilized therein capture reagent capable of binding a distinctly different probe or analyte. In this way, multiple analytes can be simultaneously detected from a single sample, the specific analyte being indicated by the position on the strip. As shown in the examples which follow, several capture sites can be formed on a single strip, each having a sequence immobilized therein which is complementary to a different analyte sequence. As the solvent front wicks up the strip, hybridization can occur at each successive site if the complementary sequences are present in the fluid. Alternatively, the sites may be oriented in the capture region parallel to the solvent front so that each is contacted by the sample simultaneously rather than successively.

Methods

Methods involving the invention comprise immobilizing a capture sequence at the capture zone of a chromatographic strip, and bringing the complementary nucleotide sequence into contact with it as the solvent fron passes through the zone. As mentioned, the complementary nucleotide sequence may be present in the solvent solution or it may be present on the strip, dried or impregnated at a probe site.

In a first method, the complementary nucleotide sequence is labeled with a radioisotope and a binary complex is formed when the complementary nucleotide sequence hybridizes with the capture sequence. In an alternative procedure, a ternary complex is formed between a capture sequence (second reagent), an analyte sequence (analyte or sample), and a labeled probe or other detection means (first reagent) for identifying the analyte or the duplex. Each of these methods is described in more detail hereinafter.

In each of the alternative methods, at least one hybridization occurs while a solution is being chromatographed or wicked up the porous medium. The complementary nucleotide sequence probes travel at or immediately behind the solvent front (herein referred to as "at" the solvent front). As a result, the length of time during which hybridization can occur depends on the time the front is in contact with the capture site (herein "front resident time"). Given a fixed size capture zone, front resident time is related by Darcy's Law to the distance between the capture zone and the first end where chromatographic transport originates. See, Ind. Enq. Chem. 61:14–28 (1969). At capture zones closer to the first end, hybridization is extremely fast, taking place in as little as 15 to 30 seconds, at least under conditions favoring rapid transport. Further up the strip, the solvent front may take as long as 5–10 minutes to cross the capture zone, providing a greater time during which hybridizations can occur. For practical strip sizes, as outlined in the examples, solvent pass time rarely exceeds 2 minutes. Even at 2 minutes, the hybridizations are occurring significantly faster than previously known methods. (See, for example, EP-A-288,737, FIG. 2, which summarizes previously known methods of hybridization and the respective times from hybridization through separation; and column 23 which states an accelerated hybridization time of 10 minutes.)

Conventional wisdom teaches that 50% efficiency is about all that can be expected from heterogeneous systems. Surprisingly, the efficiencies of hybridization using the present invention are comparable or in excess of this, provided conditions are optimized, even though the time of contact is significantly reduced. Under conditions of a large molar excess of oligonucleotide probe to immobilized target DNA (eq. about 16:1 or greater), hybridization efficiency ranges from 50 to 75% for a given probe length in the range of 30-mers. At about equimolar levels, hybridization efficiency is approximately 20%. When smaller amounts of capture sequences are used, an equimolar amount of 30-mer probe results in only approximately 4–10% hybridization efficiency. As shown in the examples, hybridization efficiency is not significantly altered by the distance of the capture zone from the origin.

According to a hybridization sandwich assay procedure of the present invention, the probe zone of the assay strip is impregnated with a complementary nucleotide sequence, which may be labelled, comprising a polynucleotide probe (first reagent) with a base sequence generally complementary to a first portion of the base sequence of an analyte nucleic acid. At the capture zone (third zone) is immobilized a capture reagent (second reagent) comprising a polynucleotide with an exposed base sequence generally complementary to a second, proximate portion of the base sequence of the analyte nucleic acid.

The analyte containing sample is applied to an intermediate zone on the strip (second zone) and is chromatographically transported to the capture zone under hybridization conditions such that analyte material is immobilized by hybridization of the second portion of its base sequence to the base sequence of the capture reagent. The complementary nucleotide sequence is then chromatographically transported under hybridization conditions to the capture zone where it is immobilized by hybridization of its base sequence with the base sequence of the first portion of the analyte molecule base sequence. The relative mobility of the sample components and the complementary nucleotide sequence or the site relationship between the intermediate zone and the capture zone is such that the analyte is disposed and immobilized against solvent transport at the capture zone prior to the complementary nucleotide sequence reaching there. Further, interfering sample components and non analyte components of the sample which are capable of reaction with the complementary nucleotide sequence are cleared from the capture zone prior to arrival of the complementary nucleotide sequence.

In an alternative sandwich assay procedure, the sample is chromatographed up the strip under hybridizing conditions to immobilized capture reagent at the capture zone and becomes immobilized there. A labeled complementary nucleotide sequence capable of detecting either the analyte sequence or double stranded sequences is then chromatographed to the capture zone and the analyte is detected. EP-A 163 220 (Miles Laboratories) describes the latter approach.

In another alternative sandwich assay procedure, sample containing analyte nucleotide sequences is mixed in solution with labeled nucleotide probes complementary to a first portion of the analyte sequence. This is done under hybridizing conditions to form labeled analyte duplexes in solution. The solution is applied to the strip by spotting, dipping or any equivalent means, and is then chromatographically transported to a zone where nucleotide complementary to a second portion of the analyte sequence is immobilized. The label is then detected.

Again, in each case at least one hybridization is occurring on the chromatographic medium at the solvent front, and the advantages of the invention are thus obtained.

Competitive hybridization assays are known in homogeneous systems (EPAA-232,967). It is also within the scope of the invention to configure a competitive heterogeneous assay using the device and methods of the present invention.

Porous Strip Materials

Porous strip materials useful with the present include those materials having capillarity and the capacity for chromatographic solvent transport of non immobilized reagents and reactive sample components by means of a selected chromatographic solvent. While a wide variety of chromatographic substrate materials such as are used for paper chromatography may be used with the invention, the use of porous media or substrates is preferred, as it improves the speed and resolution of the assays according to the invention. The materials should preferably be inert and generally not react physically or chemically with any of the analytes, reagents or reaction products. The materials may include fibrous materials suitable for use with paper chromatography techniques including woven and non woven fabrics. More preferred are those materials with microporous or microgranular structures.

Materials suitable for the present invention include granular thin layer chromatographic materials such as silica or microgranular cellulose. Preferred non granular microporous materials include microporous cellulose esters (for example, esters of cellulose with an aliphatic carboxylic acid, such as an alkane carboxylic acid, having from 1 to 7 carbon atoms, e.g., acetic acid, propionic acid, or any of the butyric acids or valeric acids); microporous nylons such as Nylon 66 (a product commercially available from DuPont, Wilminqton, Del.) and derivatives thereof; a porous polymeric membrane known as polyvinylidine difluoride (PVDF)commercially available from Millipore, Bedford, Mass. and from Pall Bioseparations Group; and derivatized paper.

Especially preferred are microporous materials made from nitrocellulose, by which term any nitric acid ester of cellulose is intended. Suitable materials include nitrocellulose in combination with any of the said carboxylic acid cellulose esters. Thus, pure nitrocellulose esters can be used as consisting of an ester of cellulose having approximately 3 nitric groups per 6 carbon atoms.

The pore size may vary within wide limits but is preferably between about 0.20 micron and 10 microns, especially between about 1 micron and 8 microns and most preferably about 5 microns. The combination of pore size and substrate thickness may be varied according to the characteristics of the specific reagents used in order to obtain desired properties of speed and resolution. As pore size increases, flow rate and kinetics also increase at the expense of hybridization efficiency and binding capacity. A most preferred medium is Schleicher & Schuell (Keene, N.H.) nitrocellulose having a pore size of 5.0 microns.

The various chromatographic materials may be used as such in suitable shapes such as films, strips or sheets, provided the supports are compatible with the solvents. They may also be coated onto or bonded or laminated to appropriate inert support materials such as paper, glass, plastic, metal or fabrics. One such inert support material is Mylar. A support material not only has the effect of providing structural support to the chromatographic material but also reduces evaporation of reagent and solvent materials during the assay procedure. The porous solid substrate is preferably in the form of strips of thickness in the range of from about 0.01 mm to about 0.5 mm, and most preferably of about 0.1 mm.

The strips may vary widely in their other dimensions but are preferably kept fairly small in order to shorten the assay development time and minimize material usage. When the strips are extremely small in size they may be attached to a suitable handle or holder in order to aid in handling and observation of results. Strips approximately 5 mm wide and up to 55 mm long have been found to be suitable in the fabrication of single pathway devices according to the present invention. Smaller strips (e.g. 35 mm long) are also possible and are preferred for minimizing cost and running time. Multiple pathway devices may utilize larger strips onto which multiple pathways are fashioned.

It is desired that in forming the shapes of the materials of the present invention that any irregularities in the materials or in the edges of the materials which might cause uneven flow through the material be avoided. Preferred means of fashioning the strip materials include the use of a paper cutter with a tungsten carbide rotary blade. Other suitable means include methods such as laser cutting which is particularly suitable for use in mass production.

Because the strip material of the device is preferably chemically inert, it may have to be activated at the capture zone in order that the capture reagent may be immobilized against solvent transport at that zone. Various methods will be required to render the capture reagent immobilized according to the particular chemical nature of the strip material and the nucleic acid. Generally, when the strip material is nitrocellulose or a mixed nitrocellulose ester no special chemical linkage is required for immobilization. Various techniques may be used for other materials and reagents which include functionalization with materials such as carbonyldiimidazole, glutaraldehyde or succinic acid, or treatment with materials such as cyanogen bromide. Other suitable reactions include Schiff base reactions and borohydride reductions of aldehydic, carbonyl and amino groups. DNA may be immobilized against solvent transport by baking onto the strip material. Baking may be carried out at temperatures ranging from about 60°

C. to about 120° C. for times varying from about 30 minutes to about 12 hours, but preferably at about 80° C. for about two hours, preceded by complete drying. It is also possible to crosslink single stranded nucleic acids to nitrocellulose by ultraviolet irradiation.

Nucleic Acid Hybridization Materials

Nucleic acid hybridization materials useful according to the present invention include RNA, DNA, cDNA and others. Typically, the materials comprise labelled and unlabelled DNA or RNA polynucleotide probes having generally complementary base sequences. The probes of the invention will generally have between about 12 and about 1,000 bases and preferably between about 12 and about 100 bases. Polynucleotides having a large number of base pairs need not be perfectly complementary to the base sequences of target gene materials and will generally hybridize provided about 70% or greater homology exists between the base sequences. However, for oligonucleotides having few bases, perfect complementarity is believed critical.

Hybridizing conditions relating to nucleotide hybridization are generally known to those of skill in the art. References include: Crosa, et al., J. Bact. 115(3), 904–911 (1973); Maniatis, et al., Molecular Cloning, Cold Spring Harbor (1982); and Current Protocols in Molecular Biology, Ausubel, et al., Eds., John Wiley & Sons (1987).

Polynucleotide probes may be obtained from universities and other institutions, and can be synthesized according to techniques well known in the art. See e.g. Caruthers, Science, 230, 281–285 (1985); Kornberg, DNA Replication, W. H. Freeman and Co., San Francisco, 670–679 (1978); Dallas, et al., J. Bacteriol. 139, 850–858 (1979) and So, et al., Nature, 277, 453–456 (1979).

Blocking Agents

Blocking agents refers to any agent which reduces background signal. Presumably, reduction in background signal is the result of reduction or elimination of nonspecific binding sites on the strip, but applicants do not wish to be bound by this theory. Unblocked nonspecific binding sites may hinder chromatographic transport of the probe or sample reagents. Blocking agents should not interfere with hybridization of the probe and capture polynucleotide, and may be applied to the strip in a pretreatment step or included in the running solvent system.

A preferred blocking agent for hybridization assays is Denhardt's solution in varying strengths. A 1× Denhardt's solution comprises 0.02% Ficoll, 0.02% polyvinylpyrrolidone and 0.2 mg/ml bovine serum albumin (BSA). Strengths of 3× to 5× Denhardt's solution (respectively, having 3 times and 5 times the concentration of 1× Denhardt's components) are useful in the present invention. A solution of 0.5 to 2.0% alkali denatured casein is also useful. A 5× Denhardt's solution is most preferred at this time. Pretreatment blocking is done by placing the strips in blocking solution in sealed bags under conditions ranging from 10–20 minutes at room temperature up to 2 hours at 65° C.

Blocking agents useful for inclusion in the running solvent system include the Denhardt's described above, sucrose solutions and polyethylene glycol (PEG) solutions. Sucrose can be used in solutions at about 1 percent. PEG ranging from 300 to 8000 MW can be used in solutions at about 5%, 300MW being preferred. A 5× Denhardt's solution is most preferred at this time.

Notwithstanding some of the following examples, salt (eg. NaCl) should not be present in pretreatment blocking solutions. Therefore, solutions such as standard saline/phosphate/ethylenediamine tetracetic acid (SSPE) are not presently preferred for pre-blocking, although they are acceptable for blocking/running solvent systems.

Solvent Systems

Suitable chromatographic solvent systems for polynucleotide hybridization assays according to the present invention include solvents capable of solubilizing the complementary nucleotide sequence and any additional reagents and materials and transporting them to the capture zone. A preferred solvent for use in polynucleotide hybridization assays comprises 5× SSPE buffer (i.e. 0.75 M NaCl, 50 mM $NaH_2PO_4$ and 5 mM EDTA (pH 7.4)), 5% PEG (MW300) and 0–50% deionized formamide. The PEG may be replaced with 5× Denhardt's solution in some cases. The preferred solvent may optionally include carrier DNA such as 100 micrograms/ml human placental DNA or salmon sperm DNA, and 0.1–0.5% SDS.

Optimization of the solvent system is important to obtain proper stringency of conditions for hybridization. The melting temperature ($T_m$) of DNA duplexes or DNA/RNA hybrids is the temperature at which the complementary strands of the duplex are 50% dissociated. $T_m$ generally increases as the number of nucleotides increases, or as the guanosine/cytosine content increases. The addition of formamide to the solvent system destabilizes the duplexes and creates conditions simulating elevated temperature. At sufficiently high formamide concentrations, no hybridization will occur. Under less stringent conditions, the formamide concentration can be optimized so that the specific desired hybridization can occur while undesirable non-specific hybridizations are inhibited or prevented. Formamide concentrations greater than about 20% eliminated non-specific hybridization signal at capture zones containing human genomic DNA as shown in the following examples. However, formamide concentrations in excess of about 40% began to have adverse effects on the nitrocellulose strips.

Detection Means

Various detection means are available for detection of the complementary nucleotide sequence bound at the capture zone. These means generally involve labelling of the complementary nucleotide sequence with a "signal" molecule capable of producing a detectable signal. The signal molecule may be directly or indirectly attached to the complementary nucleotide sequence.

Radioisotopes are particularly effective in emitting detectable signals and are useful for nucleotide hybridizations according to the invention. They are relatively small labels and can be directly attached to the complementary nucleotide sequence. Results can be autoradiographed.

Alternatively, the complementary nucleotide sequence may be labeled indirectly with a reporter compound such as biotin which, in turn, is capable of specifically binding with a signal system. Such a labeling system is disclosed in Ward, et al., U.S. Pat No. 4,711,955. Indirect signal systems comprise a detectible group conjugated to a member having one or more receptors for the reporter molecule. The detectible group can include enzyme labels, fluorescent compounds, luminescent compounds, metal chelates and colloidal particles. The member having receptors for the reporter can be any compound capable of specific interaction with the reporter, however, antibodies are preferred. For example, where biotin is the reporter, the member may be strepavidin or anti-biotin antibody.

Enzymes useful as signal systems in the present invention include alkaline phosphatase, horseradish peroxidase, glucose oxidase, $\beta$-galactosidase and $\beta$-lactamase. Other enzymes and coenzymes useful in signal producing systems include those described in U.S. Pat. No. 4,275,149 (cols. 19–23) and U.S. Pat. No. 4,318,980 (cols. 10–14) the disclosures of which are hereby incorporated by reference. The use of enzymes which produce hydrogen peroxide which then oxidizes a dye precursor to a dye is well known in the art. Suitable combinations include saccharide oxidases such as glucose oxidase and galactose oxidase and heterocyclic oxidases such as uricase and xanthine oxidase in combination with an enzyme such as peroxidase and cytochrome C oxidase to produce hydrogen peroxide and oxidize a dye precursor. The use of other oxidoreductases is also suitable as is the use of enzymes such as hydrolases and transferases. Various coenzymes such as NADH, NADPH, pyridoxal phosphate, FADH and FMNH may be used particularly in conjunction with oxidoreductases.

Finally, hybridization of the complementary nucleotide sequence to the capture sequence may be detected by means of reagents which can distinguish the duplex from single stranded nucleotides. Such reagents include anti-duplex antibodies as disclosed in EP A 163 220. These reagents may be conjugated to a detectible group as previously described.

Multiple Pathways and Solvent Barriers

Devices according to the invention may make use of single or multiple chromatographic solvent transport pathways in order to carry out a variety of assay procedures. The simplest (single pathway) devices are preferred for the present invention and are described herein.

Multiple pathway devices comprise two non coincident pathways separately leading to the capture zone. These are described in detail as the "diode", "triode" and "tetrode" devices in the copending and commonly owned parent application Ser. No. 912,878, the entire disclosure of which is incorporated herein by reference. Barriers for defining multiple pathways and means for creating them are also disclosed therein.

Throughout the examples, SSPE refers to a standard saline/phosphate buffer solution having 0.15 M NaCl, 10 mM NaH$_2$PO$_4$ and 1 mM EDTA (pH 7.4) Strengths varying from 5$\times$ to 6$\times$ were employed having, respectively, five and six times the above recited concentrations. In the examples, Denhardt's solution (1$\times$) comprises 0.02% Ficoll, 0.02% polyvinylpyrrolidone and 0.2 mg/ml BSA. Strengths of 3$\times$ to 5$\times$ Denhardt's solution were employed having, respectively, 3 times and 5 times the above recited concentrations.

EXAMPLE 1

RAPID HYBRIDIZATION OF 30mers

A. Preparation of Capture Zones on Strips

A sheet of 0.45 micron nitrocellulose membrane (Schleicher & Schuell, Keene, NH) measuring 6.3$\times$22 cm was prewet in double distilled water (15 seconds) and then soaked in 1 M ammonium acetate (1 minute). The moist membrane was placed on Whatman 3MM paper saturated in 1 M ammonium acetate and inserted into a Schleicher & Schuell Slot Blot apparatus. Double stranded plasmid DNA (pSF2001, containing an insert of the entire cryptic plasmid of *Chlamydia trachomatis*, obtained from Stanley Falkow, Stanford University) was denatured in 0.4 N sodium hydroxide at 65° C. for 60 minutes, then neutralized by addition of one volume 2 M ammonium acetate. The denatured DNA was immediately dispensed in 100 microliter aliquots each containing 12.5 fmoles pSF2001 DNA and about 0.5 microgram human genomic DNA to contiguous wells (0.75cm wide) on the assembled Slot Blot device. As a control, about 8 micrograms of human genomic DNA was denatured as above and similarly applied to the membrane via separate wells of the Slot Blot device. Mild, intermittent vacuum was applied to the device to bind DNA to the nitrocellulose. Wells were rinsed in 150 microliters 1 M ammonium acetate. The membrane was removed from the device, air dried and baked (in vacuo) at 80° C. for 2 hours to immobilize the single stranded DNA.

Strips about 0.6$\times$5.5 cm were cut from the nitrocellulose sheet such that four 'capture' zones containing immobilized capture DNA (10 fmoles pSF2001 or 6.4 micrograms human genomic) were present at approximately 14, 23, 32 and 41 mm from the first end of the strip (See FIG. 1).

B. APPLICATION OF LABELED PROBE

At a probe zone about 10 mm from the first end, all strips were impregnated with 160 fmoles each of four synthetic oligonucleotide probes (AMgen, Inc., Thousand Oaks, Calif.) which are complementary to the *C. trachomatis* cryptic plasmid DNA sequences immobilized at the capture zones on the nitrocellose strips. The sequences of the probe oligonucleotides are as follows:

a) 5' GGG TTA CAA AAG ATA CGT GAA TTC TTA AG 3'
b) TGG GAT GAT CGT AAC TCG ACT AAC CAA
c) AAA TTA ATT GCT TGT TTA ACT CCA GAA CCT
d) AAG AAC ACA TTC TTG GAA TAG CTT TGT CT

The oligomer probes were labeled at their 5'-ends with the radionuclide $^{32}$P and were applied in 0.3 microliter (0.7 $\mu$M each) of 5$\times$ Denhardt's solution. The strips were then dried 5 minutes in a mild air stream at room temperature.

C. CHROMATOGRAPHIC HYBRIDIZATION

Ascending chromatography was initiated under hybridizing conditions by dipping the first end of the uncoated strip into about 150 microliters of chromatographic solvent containing 5$\times$ Denhardt's solution, 6$\times$ SSPE, 0.1% sodium dodecyl sulfate (SDS), 100 micrograms/ml salmon sperm DNA and 20% formamide (deionized). Chromatography was run vertically at 37° C. under a glass tube to minimize solvent evaporation. Passage of the solvent front through the oligonuleotide probe zone mobilized the four oligomer probes which then migrated at the solvent front. As chromatography proceeded, the solvent front successively encountered each of the four capture zones on the strip.

As shown in FIG. 1, probes were immobilized in the central region of the capture zones by specific hybridization to complementary capture DNA sequences in the capture zone. Unreacted (i.e., nonhybridized) oligonucleotide probes were cleared from the capture zones to the top end of the strip by movement of the chromatographic solvent, thus providing an inherent wash of capture zones. The solvent front reached the top of the strip in about 30 min. The strips were then removed from the solvent reservoir, air dried and subjected to autoradiography with Kodak XAR 5 or SB 5 film.

Hybridization signals at the capture zones were quantitated either by densitometric scans of strips or liquid scintillation counting of excised capture zones. The data is summarized in Table I below. As a control, nitrocellulose strips containing human placental DNA in capture zones exhibit no hybridization signal at capture zones when chromatographed under identical experimental conditions.

D. HYBRIDIZATION KINETICS AND EFFICIENCY

The time of interaction between probes at the solvent front and capture DNA in the capture zone was observed to be about 0.2–2 minutes. This is dependent upon solvent viscosity, nitrocellulose porosity and distance of the capture zone from the first end of the strip according to Darcy's Law.

Table I shows the experimental hybridization efficiencies obtained. Under the conditions described above for molar excess of probe to capture DNA, the efficiency of DNA:DNA hybridization is not significantly altered by the distance between probe zone and capture zone.

DNA (about 5 micrograms), denatured in alkali as described in Example 1, was applied in a similar manner to adjacent wells. Therefore, each strip comprised one specific capture zone and one control capture zone at about 18 and 27 mm, respectively, from the first end of the strip.

An oligonucleotide probe (ie., a 74-mer) complementary to the universal cloning site of M13mp18(+) was synthesized using known techniques. See, for example, Caruthers, Science 230: 281–285 (1985). The nucleotide sequence was as follows:

5' CGG CCA GTG CCA AGC TTG CAT GCC TGC AGG TCG ACT CTA
GAG GAT CCC CGG GTA CCG AGC TCG AAT TCG TAA TC 3'

The probe DNA (150 fmoles) is applied in 0.3 microliter 5× Denhardt's solution about 10 mm from the first end of the strip. The strip was immediately dipped in 150 microliter chromatographic solvent comprising 5% polyethylene glycol (MW 300), 6× SSPE (pH 7.4), 0.1% SDS and 30–50% formamide. Strips were developed at ambient temperature under inverted glass tubes as in Example 1. Chromatography terminated upon arrival of the solvent front at the top end of the strip, ie. about 10 min. Again, the signal was independent of the capture zone position, showing very rapid hybridization kinetics. Comparable hybridization efficiencies are obtained with the 5 micron strips of this example, as with the 0.45 micron membrane of Example 1, in spite of the fact that chromatographic flow is approximately 6 times more rapid through the larger pores.

EXAMPLE 3

SPECIFICITY OF 12 mers ON A MULTIPLE CAPTURE ZONE STRIP

In this example, complementary DNA (cDNA, 1.2 kilobases) of the ornithine transcarbamylase (OTC) gene from either a wild type (wt) or sparse fur (spf)

TABLE I

EFFICIENCY OF HYBRIDIZATION

| Capture DNA: | 10 fmoles pSF2001 applied/Capture Zone | | | | |
| --- | --- | --- | --- | --- | --- |
| Nonspecific Capture DNA: | 6.4 micrograms Human genomic DNA/Capture Zone | | | | |
| Probe DNA: | 157 fmoles each of four [$^{32}$P]oligonucleotides (27- to 30-mers) | | | | |
| Specific Activity: | $2.6 \times 10^3$ cpm/fmole | | | | |
| | Capture* | | Probe** | | Observed |
| Capture Zone | DNA (fmoles) | Probe:Target* | Hybridized (fmoles) | Expected** cpm | Observed cmp | Expected expressed as % |
| 1 | 4.2 | 37.5:1 | 16.8 | 43500 | 31191 | 71.7 |
| 2 | 5.8 | 27.1:1 | 23.2 | 60000 | 37160 | 61.9 |
| 3 | 6.7 | 23.5:1 | 26.8 | 69400 | 53108 | 76.5 |
| 4 | 7.2 | 21.9:1 | 28.8 | 74600 | 63233 | 84.8 |

*The amount of capture DNA exposed to migrating oligonucleotides at each capture zone is a fraction of the 10 fmoles of applied capture DNA as calculated using the width of the observed signal bar.
**At 100% hybridization efficiency.

EXAMPLE 2

RAPID HYBRIDIZATION OF 74mers

Conditions for uniform migration and rapid hybridization of 74mers are similar to that described in EXAMPLE 1 with the exception of the variations described in this example. Untreated, dry 5.0 micron nitrocellulose membrane was impregnated with capture DNA in a Slot Blot device as before. Single stranded capture DNA (50 fmoles of M13mp18(+), Pharmacia LKB) was applied in about 10 microliters of a sodium hydroxide and ammonium acetate solution to selected wells of the Slot Blot device. A control DNA, human genomic mouse was cloned into the plasmid pTZ19R (Pharmacia, LKB) by C. Thomas Caskey et al., Baylor College of Medicine, Houston, Tex. The recombinant plasmids were denatured in 0.4 N sodium hydroxide and neutralized in 2 M ammonium acetate. About 40 fmoles DNA were applied to the capture zones of a strip as shown in FIGS. 2A and 2B. Each strip was configured to have three capture zones containing: 1) cloned cDNA from wt mutant mice; 2) cloned cDNA from spf mutant mice; and 3) plasmid pBR322 DNA, located at 18, 27 and 36 mm, respectively, from the bottom or first end of the strip (FIG. 2).

Allele specific oligonucleotide (ASO) probes complementary to either the wt or spf capture DNA and labeled with $^{32}P$ were synthesized by C. Thomas Caskey, Baylor College of Medicine, Houston. The nucleotide sequences were as follows:

a) 5' CAA GTG AAT GTC 3' = wt probe
(perfect match for wild-type OTC cDNA)

b) 5' CAA GTT AAT CTC 3' = spf probe
(perfect match for sparse fur OTC cDNA)

The two ASO probes differ from each other by only a single nucleotide at an internal position (ie., G or T at the 6th base pair from the 5' end). The wt probe (50 fmoles) was applied in 0.3 microliter 5X Denhardt's solution at a probe zone about 10 mm from the bottom of strip 2A (see FIG. 2). The spf probe (50 fmoles) was similarly applied to the other strip (FIG. 2B). Conditions were as in Example 1 except that chromatography was in 5% polyethylene glycol (300 MW) and 6X SSPE (pH 7.4) at ambient temperature.

As shown in FIG. 2, strip 2A, containing radiolabeled wt probe, shows a specific hybridization signal at the first capture zone (containing wt cDNA but not at the spf or pBR322 (control) zones. Strip 2B, chromatographed with the radiolabeled spf probe, shows a specific hybridization signal at the spf and pBR322 DNA capture zones but not the wt capture zone. A fortuitous perfect match between the first nine 3' end nucleotides of the spf 12 mer and two distinct nine nucleotide stretches in the pBR322 DNA sequence accounts for the "cross hybridization" between these two DNAs as follows:

A) PBR322 DNA (pos. #1969): 5'...GACATTAACgct...3'
      spf probe: 3'   CTGTAATTGaac   5'

B) PBR322 DNA (pos. #4311): 5'...GACATTAACcTa...3'
      spf probe: 3'   CTCTAATTGaAc   5'

A single internal base pair mismatch between wt 12-mer and the two pBR322 DNA sequences above is sufficient to destabilize the 12 base pair duplex as shown:

PBR322 DNA (pos. #1969): 5'...GACATTaACgct...3'
      wt probe:   3'   CTGTAAgTGaac   5'

Therefore, a hybridization signal is not detected at the third (pBR322) capture zone on Strip 2A.

An exquisite degree of specificity is therefore achieved in the chromatographic hybridization format when chromatographing ASO probes (about 12 nucleotides) at ambient temperature under hybridization conditions. Observed hybridization efficiencies of less than 1% of theoretical in this example may be attributed to the relatively high instability (low $T_m$) of short DNA duplexes (i.e., about 12 base pairs).

This example also demonstrates the ability to place multiple capture zones on a single strip, each zone having immobilized therein a capture sequence for a different complementary sequence. The capture sequences will hybridize with and immobilize only those probe sequences having sufficient homology.

EXAMPLE 4

EFFECT OF PROBE DNA RESIDENT TIME ON HYBRIDIZATION

In this example, a sheet of 0.45 micron nitrocellulose membrane (S & S) measuring 6.3×22 cm was prewet in double distilled water, then 1 M ammonium acetate and then placed in a Slot Blot apparatus as described in Example 1. Plasmid pSF2001, containing an insert of *C. trachomatis* cryptic plasmid DNA, was denatured and neutralized (Example 1) immediately preceding application to the membrane. The denatured DNA was dispensed in about 120 microliter aliquots, each containing 62 fmoles pSF2001 DNA and about 1 microgram human placental DNA, to wells (0.75 cm. wide) of the Slot Blot device. As a control, about 6 micrograms of human placental DNA was denatured as described above and then applied to independent wells of the Slot Blot device to serve as nonspecific capture DNA control. DNA was adsorbed to the membrane by applying an intermittent mild vacuum, followed by a 100 microliter rinse of each well with 1 M ammonium acetate. DNA was immobilized by baking the membrane at 80° C. for 2.4 hours.

As shown in FIGS. 3A and 3B, strips measuring 0.6×5.3 cm. ('long') or 0.6×3.7 cm. ('short') were cut from the membrane such that each strip contained two capture zones with denatured pSF2001 DNA. The first and second capture zones [18(1) and 18(2)] were 2.5 and 1.7 cm., respectively, from the top (16) of both strips so that the distance from the bottom end (14) to the first capture zone varied between the short and long strips.

At a probe zone (22) located 0.4 cm. below the first capture zone, the strips were impregnated with about 60 fmoles each of four $^{32}P$-labeled oligonucleotides (as in Example 1) complementary to the immobilized pSF2001 DNA. The probe DNA was applied to strips in 0.3 microliters 5× Denhardt's solution and dried 3 minutes in a mild air stream.

The bottom end (14) was dipped in a running buffer (20) similar to that described in Example 1 (with the exception of the absence of carrier DNA) to initiate ascending chromatography. Passage of the solvent front through the probe zone solubilized and mobilized the probe DNA. The probe DNA, present at the solvent front, migrated through the central region (about 2 mm. wide) of both capture zones. Therefore, the effective probe:capture DNA ratio in this region of the capture zone is calculated (as in Table I) to range from 3.2:1 to 4.5:1. Based upon Darcy's Law, the resident times of probe DNA at capture zones were calculated and determined to represent the time from the initial contact of the probe with the bottom edge of the capture zone to the departure of unreacted probe DNA at the top edge of the capture zone (Table II).

Chromatography was stopped upon arrival of the solvent front at the top end (16) of the strip (i.e., developing times of about 27 min. for 'long' strips and about 13 min. for 'short' strips). Chromatograms were subjected to autoradiography. Hybridization at capture zones was quantitated by liquid scintillation counting.

Efficiencies of hybridization at capture zones were calculated based upon the number of observed counts divided by the expected counts (at 100% hybridization efficiency in the contact area) in a manner similar to that described in Table I. Comparison of signals at corresponding capture zones of 'long' and 'short' strips revealed comparable efficiencies (Table II) despite differences in solvent front flow rate (i.e. resident time) through corresponding capture zones. The data from Table II is represented graphically in FIG. 4.

TABLE II

Effect of Solvent Flow Rate on Hybridization Efficiency

| | Capture Zone #1 | | Capture Zone #2 | |
|---|---|---|---|---|
| | *Probe Resident Time (min.) | **Observed cpm Expected cmp (expressed as %) | *Probe Resident Time (min.) | **Observed cpm Expected cpm (expressed as %) |
| Long Strips (0.6 × 5.3 cm.) | 1.6 | 32.9 ± 2.0 | 2.2 | 34.8 ± 1.2 |
| Short Strips (0.6 × 3.7 cm.) | 0.8 | 26.9 ± 1.8 | 1.3 | 32.7 ± 1.4 |

*Calculated using Darcy's Law for behavior of solvent front migration on a porous solid support
**Average of triplicate samples ± s.d.

EXAMPLE 5

STRIP HYBRIDIZATION ASSAY FOR CHLAMYDIAL DNA (Formamide Titration)

In this example, a single pathway polynucleotide hybridization assay devices were constructed of microporous (0.45 micron) nitrocellulose material approximately 5 mm wide by 55 mm long with a thickness of approximately 0.1 mm. To a capture zone approximately 23 mm from the first end of the strip (corresponding to the third zone) was applied about 1.5 microliters of a capture reagent solution comprising about 5 fmoles linearized, heat-denatured DNA (recombinant plasmid containing C. trachomatis cryptic plasmid insert as in Example 1) in 50 mM $NaH_2PO_4$ buffer (pH 7.4) and 2mM EDTA. As a control, 10 micrograms of human genomic DNA was applied in identical manner to capture zones on separate strips. The strips were then air dried and baked at 80° C. for 2 hours.

Strips containing the capture reagent were then impregnated with a blocking solution of 50 mM $NaH_2PO_4$ and 2 mM EDTA by placing them in a sealed bag for 30 minutes at 37° C., followed by air drying.

At a probe zone about 7 mm from the first end, the strips were impregnated with 0.5 microliter of a solution containing 50 mM $NaH_2PO_4$, 2 mM EDTA and about 50 fmoles of each of four $^{32}P$-labeled oligonucleotides (27–30mers) having nucleotide sequences generally complementary to a portion of the nucleotide sequence of capture reagent. Each of the complementary nucleotide sequences was labelled at its 5' end by treatment with $^{32}P$ radiolabel and T4 polynucleotide kinase. The complementary nucleotide sequence material was air dried to the probe zone on all the strips.

Assays were conducted by dipping the device into about 175 microliters of chromatographic solvent comprising 5× SSPE solution, 3× Denhardt's solution and varying concentrations (i.e. 0–40%) deionized formamide. While the strips were incubated at 37° C. the solvent progressed upward along the device to solubilize and chromatographically transport the complementary nucleotide sequence toward the capture zone.

Upon reaching the capture zone, complementary nucleotide sequence was immobilized by hybridization to complementary nucleotide sequences of the capture reagent immobilized at that zone. Any non hybridized material is cleared from the capture zone by chromatographic solvent transport. The strips and chromatographic solvent were incubated at 37° C. until the solvent front reached the top of the strip at which time the strip was removed from the solvent and air dried. The strip was subjected to autoradiography with Kodak XAR-5 film. Exposure of the film revealed hybridization signal at the corresponding location on the strip.

As a result of the varying formamide concentrations it was found that 20% or greater concentrations eliminated the hybridization signal at control (human genomic DNA) capture zones.

EXAMPLE 6

SANDWICH HYBRIDIZATION ASSAY

In this example, a single pathway polynucleotide hybridization assay device is constructed and used. A piece of microporous nitrocellulose material approximately 5 mm wide by 55 mm long with a thickness of approximately 0.1 mm is cast onto an inert Mylar support sheet approximately 0.1 mm thick. The strip is prewetted with 5× SSPE buffer solution (pH 7.4). To a capture zone approximately 27 mm from the first end of the strip is applied about 1.5 microliters of a capture reagent solution comprising about 15 fmoles linearized, heat denatured DNA generally complementary to a first portion of the nucleotide sequence of the analyte polynucleotide in 5× SSPE buffer (pH 7.4). The strip is then air dried and baked at 80° C. for 2 hours.

The strip material to which the capture reagent has been applied is then prewetted in the 5× SSPE buffer solution and impregnated with a blocking solution comprising 5× SSPE buffer and 5× Denhardt's solution. The strip is placed in a sealed bag for 2 hours at 65° C and is then air-dried.

The strip is then impregnated at the probe zone 7 mm from the first end with about 100 fmoles of a complementary nucleotide sequence material comprising a linearized, denatured polynucleotide with a nucleotide sequence generally complementary to a second portion of the nucleotide sequence of the analyte polynucleotide. The complementary nucleotide sequence is labelled at its 5' end by treatment with $^{32}P$ radiolabel and T4 polynucleotide kinase. The complementary nucleotide sequence material is then air dried and a Mylar cover plate with a gap over a second zone between the first and capture zones is placed over the nitrocellulose chromatographic material.

Assays are conducted with the polynucleotide hybridization assay device of the invention by application of analyte containing sample material to the second zone. A cover tab is then placed over the second zone and the assay device is dipped into about 175 microliters of chromatographic solvent comprising 5× SSPE buffer (pH 7.4), 3× Denhardt's solution and 50% deionized formamide. While the strip is incubated at 37° C.

(vertically under a glass tube) the solvent progresses upward along the device and solubilizes and chromatographically transports the complementary nucleotide sequence toward the capture zone. Upon reaching the second zone the chromatographic solvent solubilizes and transports the analyte containing sample toward the capture zone. The relative mobility of the complementary nucleotide sequence and the sample components is such that the analyte is disposed and immobilized against solvent transport at the capture zone prior to the complementary nucleotide sequence reaching the capture zone. Further, any interfering sample components and unhybridized components of the sample which are capable of reaction with the complementary nucleotide sequence are cleared from the capture zone prior to chromatographic transport of the complementary nucleotide sequence to the capture zone.

Upon reaching the capture zone, any analyte material within the sample will be immobilized by hybridization at a second nucleotide sequence with the capture reagent immobilized at that zone. Any non-hybridized material will be cleared from the capture zone by chromatographic solvent transport prior to arrival of the complementary nucleotide sequence. Upon reaching the capture zone, the radiolabelled complementary nucleotide sequence will itself be immobilized by hybridization with a first nucleotide sequence of the analyte. The strip and chromatographic solvent are incubated at 37° C. until the solvent front reaches the top of the strip at which time the strip is removed from the solvent and air dried. The strip is then subjected to autoradiography with Kodak XAR-5 film. The presence of analyte in the sample material will be indicated by exposure of film contacted at the capture zone. Variations of the device of this example include "diode", "triode" and "tetrode" devices utilizing enzyme labels and detection systems.

EXAMPLE 7

IMPROVED SANDWICH HYBRIDIZATION ASSAY

Example 6 is repeated except as follows. Additional strips are prepared as a control and contain at their capture zones about 2 micrograms of human genomic DNA. The strips are prewetted in solutions which do not contain a NaCl component, eg. glass distilled water, or 5× Denhardt's solution or 5× PE (ie. SSPE less NaCl). The strip is blocked with 5× Denhardt's solution or 0.5-2.0% alkali-denatured casein. At the probe zone, about 100 fmoles of each of four oligonucleotides is applied to the strips as in Example 1. The running solvent system employs 20 to 40% formamide.

Numerous modifications and variations in practice of the invention are expected to occur to those skilled in the art upon consideration of the foregoing descriptions of preferred embodiments thereof. Consequently, only such limitations should be placed on the invention as appear in the following claims.

What is claimed is:

1. A device for performing solid phase hydridizations of soluble, single-stranded polynucleotides, comprising a strip of porous chromatographic medium having:
   a contact site at or near one end;
   a capture site remote from the contact side whereat a single-stranded target polynucleotide complementary to a labelled, soluble polynucleotide is immobilized against transport or becomes immobilized against transport by binding to a capture polynucleotide which itself is immobilized against transport;
   said labelled polynucleotide dried on the medium at a location between the contact site and the remote capture site, such that it can be mobilized and transported to the remote capture site by a transport solution; and
   capillary means for transporting a solution containing the labelled, soluble polynucleotide under hydridizing conditions to the remote capture site, whereby hybridization can occur between complementary base pairs of the polynucleotides;
   wherein said strip further comprises a first region, said first region being substantially devoid of capture polynucleotide, adjacent said capture site in the direction of said contact site and a second region adjacent said capture site in the opposite direction, and wherein said strip is nonsegmented between said first region and said capture site and between said second region and said capture site.

2. A device according to claim 1, wherein the porous medium comprises a strip of nitrocellulose having a pore size of between about 0.2 micron and about 10 microns.

3. A device according to claim 2 wherein the nitrocellulose has a pore size of about 5.0 microns.

4. A device according to claim 1 wherein said capillary means continues beyond the second region to remove unhybridized polynucleotides and other nonreactive solution components from the remote site.

5. A device according to claim 1 wherein said capillary means transports said solution at a rate such that a solution front containing said labelled polynucleotide contacts the remote capture site for less than about 10 minutes.

6. A device according to claim 1 wherein said capillary means transports said solution at a rate such that said solution front contacts the remote site for less than about 2 minutes.

7. A method of detecting the presence of a target polynucleotide comprising:
   a) providing a porous medium capable of transporting by capillarity a solution of single stranded polynucleotides, said medium having a contact site at or near one end and a capture site remote from the contact site, wherein said strip further comprises a first region, said first region being substantially devoid of capture polynucleotide, adjacent said capture site in the direction of said contact site and a second region adjacent said capture site in the opposite direction, and wherein said strip is nonsegmented between said first region and said capture site and between said second region and said capture site;
   b) immobilizing a sample suspected to contain target polynucleotide in single-stranded form at said capture site;
   c) under hybridizing conditions, contacting the contact site with either:
      i) a transport solvent containing a labelled single-stranded polynucleotide complementary to said target polynucleotide; or
      ii) a transport solvent capable of mobilizing a labelled single-stranded polynucleotide complementary to said target polynucleotide, said labelled polynucleotide having been previously dried onto a probe site located intermediate the contact site and the remote capture site such that it can be mobilized by transport solvent, the labeled polynucleotide being transported by capillarity to the remote capture site;

d) prior to or during step c), blocking nonspecific binding sites on said porous medium; and e) detecting the presence of label, if any, at said remote capture site as a measure of the target polynucleotide.

8. The method according to claim 7, wherein the contact site is contacted with a transport solvent containing the labelled single-stranded polynucleotide complementary to said target polynucleotide.

9. The method according to claim 7, including an additional step, prior to step c, of drying a labelled single-stranded complementary polynucleotide onto the medium at a location between the contact site and the remote site, such that the complementary polynucleotide can be mobilized and transported by the transport solvent, and contacting the contact site with a transport solvent capable of mobilizing the dried single-stranded complementary polynucleotide as recited in step c) ii) of claim 7.

10. A method according to claim 7 wherein the solution containing the labelled polynucleotide is transported through the medium at a rate such that the labelled polynucleotide contacts the remote site for less than about 5 minutes.

11. A method according to claim 9 wherein the solution containing the complementary polynucleotide is transported through the medium at a rate such that said solution front contacts the remote capture site for less than about 2 minutes.

12. A method according to claim 7 wherein transport of solution continues past the second region to remove unhybridized polynucleotides and other non-reactive solution components from the remote capture site.

13. A method according to claim 7 wherein the porous medium comprises a strip of nitrocellulose having a uniform pore size between about 0.1 micron and about 10 micron.

14. A method according to claim 7 wherein step d) is performed by pretreating the medium with a blocking agent before contacting it with the transport solvent.

15. A method according to claim 7 wherein step d) is performed by incorporating a blocking agent into the transport solvent.

16. A method of detecting the presence of a target polynucleotide comprising:

a) providing a porous medium capable of transporting by capillarity a solution of single stranded polynucleotides, said medium having a contact site at or near one end, and having immobilized at a capture site remote from said contact site, a single-stranded polynucleotide (capture probe) capable of hybridizing to a first portion of a complementary target polynucleotide, wherein said medium further comprises a first region, said first region being substantially devoid of capture polynucleotide, adjacent said capture site in the direction of said contact site and a second region adjacent said capture site in the opposite direction, and wherein said strip is nonsegmented between said first region and said capture site and between said second region and said capture site;

b) causing a sample suspended to contain target polynucleotide to contact said remote capture site, directly or by solvent transport, under hybridizing conditions to permit hybridization of the capture probe with the first portion of any target polynucleotide present;

c) during or after step b), contacting the contact site under hybridizing conditions with either:

i) a transport solvent containing a labelled single-stranded polynucleotide complementary to a second, distinct portion of said target polynucleotide; or ii) a transport solvent capable of mobilizing a labelled single-stranded polynucleotide complementary to a second distinct portion of said target polynucleotide, said labelled polynucleotide having been previously dried onto a probe site located intermediate the contact site and the remove capture site such that it can be mobilized by transport solvent, the labelled polynucleotide being transported by capillarity to the remote capture site to form a ternary complex of capture probe:target polynucleotide:labelled probe in the presence of target polynucleotide;

d) prior to or during step c), blocking nonspecific binding sites on said porous medium; and e) detecting the presence of label, if any, at said remote capture site as a measure of the target polynucleotide.

17. The method according to claim 16, wherein the contact site is contacted with a transport solvent containing the labelled single-stranded polynucleotide complementary to said target polynucleotide.

18. The method according to claim 16, wherein the contact site is contacted with a transport solvent capable of mobilizing the labelled single-stranded polynucleotide complementary to said target polynucleotide; including an additional step, prior to step d, of drying the single-stranded complementary polynucleotide onto the medium at a location between the contact site and the remote site, such that the complementary polynucleotide can be mobilized and transported by the transport solvent.

19. A method according to claim 16 wherein the solution containing the labelled polynucleotide is transported through the medium at a rate such that the labelled polynucleotide contacts the remote site for less than about 5 minutes.

20. A method according to claim 18 wherein the solution containing the complementary polynucleotide is transported through the medium at a rate such that said solution front contacts the remote capture site for less than about 2 minutes.

21. A method according to claim 16 wherein transport of solution continues past the second region to remove unhybridized polynucleotides and other non-reactive solution components from the remote capture site.

22. A method according to claim 16 wherein the porous medium comprises a strip of nitrocellulose having a uniform pore size between about 0.1 micron and about 10 microns.

23. A method according to claim 16 wherein step d) is performed by pretreating the medium with a blocking agent before contacting it with the transport solvent.

24. A method according to claim 16 wherein step d) is performed by incorporating a blocking agent into the transport solvent.

25. A method of detecting the presence of a target polynucleotide comprising:

a) providing a porous medium capable of transporting by capillary a solution of single-stranded polynucleotides, said medium having a contact site at or near one end, and having immobilized at a capture site remote from said contact site, a single-stranded polynucleotide (capture probe) capable of hybridizing to a complementary target polynucleotide, wherein said medium further comprises a first region, said first region being substantially devoid of capture polynucleotide, adjacent said capture site in the direction of said contact site and a second region adjacent said capture site in the opposite direction, and wherein said strip is nonsegmented between said first region and said capture site and between said second region and said capture site;

b) labelling any target polynucleotide present in a test sample with a detectable label;

c) contacting the contact site under hybridizing conditions with either;
  i) a transport solvent containing said test sample suspected to contain said labelled target polynucleotide; or
  ii) a transport solvent capable of mobilizing a test sample suspected to contain said labelled target polynucleotide, said test sample having been previously dried onto a probe site located intermediate the contact site and the remote capture site such that it can be mobilized by transport solvent, the labelled polynucleotide being transported by capillarity to the remote capture site;

d) prior to or during step c), blocking nonspecific binding sites on said porous medium; and e) detecting the presence of label, if any, at said remote capture site as a measure of the target polynucleotide.

26. The method according to claim 25, wherein the contact site is contacted with a transport solvent containing the labelled single-stranded polynucleotide complementary to said target polynucleotide.

27. The method according to claim 25, wherein the contact site is contacted with a transport solvent capable of mobilizing the labelled single-stranded polynucleotide complementary to said target polynucleotide; including an additional step, prior to step d, of drying the single-stranded complementary polynucleotide onto the medium at a location between the contact site and the remote site, such that the complementary polynucleotide can be mobilized and transported by the transport solvent.

28. A method according to claim 25 wherein the solution containing the labelled polynucleotide is transported through the medium at a rate such that the labelled polynucleotide contacts the remote site for less than about 5 minutes.

29. A method according to claim 27 wherein the solution containing the complementary polynucleotide is transported through the medium at a rate such that said solution front contacts the remote capture site for less than about 2 minutes.

30. A method according to claim 25 wherein transport of solution continues past the second region to remove unhybridized polynucleotides and other non-reactive solution components from the remote capture site.

31. A method according to claim 25 wherein the porous medium comprises a step or nitrocellulose having a uniform pore size between about 0.1 micron and about 10 microns.

32. A method according to claim 25 wherein step d) is performed by pretreating the medium with a blocking agent before contacting it with the transport solvent.

33. A method according to claim 25 wherein step d) is performed by incorporating a blocking agent into the transport solvent.

34. In a solid phase hybridization method for detecting the presence of a target polynucleotide involving:
  immobilizing a target polynucleotide, if present in a test sample, directly or via an intermediate capture structure, on a solid phase at a capture site; before, during or after said immobilization, attaching a detectable label to said target polynucleotide, if present; and detecting said label, if any, at said capture site; the improvement comprising:
  a) using a porous chromatographic medium as said solid phase, said medium having a contact site at one end and said capture site being remote from said contact site, wherein said medium further comprises a first region, said first region being substantially devoid of capture polynucleotide, adjacent said capture site in the direction of said contact site and a second region adjacent said capture site in the opposite direction, and wherein said strip is nonsegmented between said first region and said capture site and between said second region and said capture site, and optionally including at least one other site intermediate said contact site and said capture site; and
  b) performing at least one of said immobilizing and attaching steps by immobilizing at least one single-stranded polynucleotide in hybridizable form at said capture site and transporting by chromatographic solvent transport from said contact site or said other site at least one single-stranded labelled complementary polynucleotide capable of hybridizing with said immobilized polynucleotide, such that label becomes immobilized at said capture site if target polynucleotide is present;
  wherein at least one hybridization step occurs between an immobilized polynucleotide on said solid phase and a complementary polynucleotide in a mobile phase transported past said immobilized polynucleotide by chromatographic solvent transport.

* * * * *